(12) United States Patent
Wang

(10) Patent No.: US 11,206,835 B2
(45) Date of Patent: Dec. 28, 2021

(54) AIR PURIFICATION COMPOSITION WITH ANTIVIRAL AND BACTERICIDAL FUNCTIONS

(71) Applicant: Jingning Wang, Huizhou (CN)

(72) Inventor: Jingning Wang, Huizhou (CN)

(73) Assignee: Guorun Biotechnology (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 16/620,271

(22) PCT Filed: Aug. 28, 2018

(86) PCT No.: PCT/CN2018/102629
§ 371 (c)(1),
(2) Date: Dec. 6, 2019

(87) PCT Pub. No.: WO2020/015053
PCT Pub. Date: Jan. 23, 2020

(65) Prior Publication Data
US 2020/0329717 A1 Oct. 22, 2020

(30) Foreign Application Priority Data
Jul. 16, 2018 (CN) .......................... 201810777545.1

(51) Int. Cl.
| | | |
|---|---|---|
| *A01N 65/48* | (2009.01) | |
| *A01N 65/08* | (2009.01) | |
| *A01N 65/12* | (2009.01) | |
| *A01N 65/20* | (2009.01) | |
| *A01N 65/28* | (2009.01) | |
| *A61L 9/04* | (2006.01) | |
| *B01D 11/02* | (2006.01) | |
| *B01D 53/14* | (2006.01) | |
| *A61L 101/46* | (2006.01) | |
| *A61L 101/40* | (2006.01) | |

(52) U.S. Cl.
CPC ............ *A01N 65/48* (2013.01); *A01N 65/08* (2013.01); *A01N 65/12* (2013.01); *A01N 65/20* (2013.01); *A01N 65/28* (2013.01); *A61L 9/042* (2013.01); *A61L 9/044* (2013.01); *B01D 11/0288* (2013.01); *B01D 53/1487* (2013.01); *B01D 53/1493* (2013.01); *A61L 2101/40* (2020.08); *A61L 2101/46* (2020.08); *B01D 2252/20* (2013.01)

(58) Field of Classification Search
None
See application file for complete search history.

(56) References Cited

U.S. PATENT DOCUMENTS

| | | |
|---|---|---|
| 4,892,719 A | 1/1990 | Gesser |
| 5,009,239 A | 4/1991 | Cohen et al. |
| 2013/0213229 A1 | 8/2013 | Shahin et al. |

FOREIGN PATENT DOCUMENTS

| | | |
|---|---|---|
| CN | 102559408 A | 7/2012 |
| CN | 104450257 A | 3/2015 |
| CN | 104645800 A | 5/2015 |
| CN | 105238583 A | 1/2016 |
| CN | 106259549 A | 1/2017 |
| CN | 106310906 A | 1/2017 |
| CN | 106342946 A | 1/2017 |
| CN | 106366308 A | 2/2017 |
| CN | 108158869 A | 6/2018 |
| WO | 2018024087 A1 | 2/2018 |
| WO | 2018028275 A1 | 2/2018 |

OTHER PUBLICATIONS

PCT; App No. PCT/CN2018/102629; International Search Report dated Mar. 14, 2019.
Talaiekhozani, Amirreza, et al., "Investigation of formaldehyde removal from synthetic contaminated air by using human hair," Environmental Health Engineering and Management Journal, vol. 3, No. 4, Sep. 28, 2016, pp. 191-196, XP055753937.

*Primary Examiner* — Melissa L Fisher
(74) *Attorney, Agent, or Firm* — Fitch, Even, Tabin & Flannery, LLP

(57) ABSTRACT

Disclosed is a novel air purification composition with antiviral and bactericidal functions, the composition at least comprising the following components in percentage by weight: 0.3%-1% of a black poplar essential oil, 0.1%-1% of a tea tree essential oil, 0.1%-0.5% of a *Cupressus funebris* essential oil, 0.1%-1% of an *Artemisia apiacea* essential oil, 0.1%-10% of a *Sophora flavescens* extract, 0.1%-5% of a ginger extract, 5%-30% of a *Cupressus funebris* hydrolate, 0.5%-1% of a hyperbranched amino polymer, 0.5%-5% of a surfactant, and the balance being water.

10 Claims, No Drawings

AIR PURIFICATION COMPOSITION WITH ANTIVIRAL AND BACTERICIDAL FUNCTIONS

TECHNICAL FIELD

The present invention relates to the field of environmental health, and in particular to a novel air purification composition with antiviral and bactericidal functions.

BACKGROUND ART

With the improvement of living standards, more and more attention is paid to pollutions caused by decoration. Especially in newly decorated houses, pollutants such as formaldehyde severely exceed standards and affect people's health, and therefore, some air fresheners are needed to remove these pollutants.

There are several types of air purifiers below: 1. adsorption-type air purifiers, such as activated carbon, bamboo charcoal and coconut charcoal; and 2. masking deodorant products, such as condensation-off pomanders and air fresheners, i.e. purification products that can remove pollutants by using physical, chemical, oxidation, catalytic oxidation, and reduction properties of activated carbon. Air fresheners do not eliminate odors, but merely mask the odors.

SUMMARY OF THE INVENTION

In order to solve the problems of the prior art, the present invention provides a novel air purification composition with antiviral and bactericidal functions, which at least comprises the following components in percentage by weight: 0.3%-1% of a black poplar essential oil, 0.1%-1% of a tea tree essential oil, 0.1%-0.5% of a *Cupressus funebris* essential oil, 0.1%-1% of an *Artemisia apiacea* essential oil, 0.1%-10% of a *Sophora flavescens* extract, 0.1%-5% of a ginger extract, 5%-30% of a *Cupressus funebris* hydrolate, 0.5%-1% of a hyperbranched amino polymer, 0.5%-5% of a surfactant, and the balance being water.

In some embodiments, it at least comprises the following components in percentage by weight: 0.5%-0.8% of a black poplar essential oil, 0.4%-0.6% of a tea tree essential oil, 0.2%-0.4% of a *Cupressus funebris* essential oil, 0.5%-0.8% of an *Artemisia apiacea* essential oil, 4%-8% of a *Sophora flavescens* extract, 2%-4% of a ginger extract, 14%-22% of a *Cupressus funebris* hydrolate, 0.8%-1% of a hyperbranched amino polymer, 2%-6% of a surfactant, and the balance being water.

In some embodiments, it at least comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

In some embodiments, the weight ratio of said ginger extract to said *Sophora flavescens* extract is 1:2.

In some embodiments, a method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness.

In some embodiments, the weight ratio of said clear limewater to said *Sophora flavescens* is 6:1.

In some embodiments, a method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness.

In some embodiments, said surfactant is a mixture of a non-ionic surfactant and an anionic surfactant.

In some embodiments, said nonionic surfactant is selected from at least one of Tween-20, Tween-40 and Tween-60.

In some embodiments, said anionic surfactant is selected from one of sodium dodecyl sulfonate and potassium dodecyl sulfonate.

DETAILED DESCRIPTION OF EMBODIMENTS

For a better understanding of the content of the present invention, reference can be made to the detailed description of preferred embodiments of the present invention below and examples included therein. Unless defined otherwise, all the technical and scientific terms used herein have the same meanings as are commonly understood by a person of ordinary skill in the art. In case of contradiction, the definitions in the description shall prevail.

As used herein, the term "prepared from" is synonymous with the term "comprising". As used herein, the terms "comprise", "include", "have", "contain", or any other variants thereof, are intended to cover non-exclusive inclusion. For example, compositions, steps, methods, articles of manufacture or devices that contain listed elements are not necessarily limited to those elements but may include other elements not expressly listed or elements inherent to such compositions, steps, methods, articles of manufacture or devices.

The conjunction "consisting of" excludes any unspecified elements, steps or components. If used in a claim, this phrase will make said claim closed so that this phrase excludes materials other than those materials described, but conventional impurities related thereto are excepted. When the phrase "consisting of" appears in a clause of the main body of a claim, but does not immediately follows the subject matter thereof, it is limited to only the elements described in the clause; other elements are not excluded from said claim as a whole.

When equivalents, concentrations, or other values or parameters are expressed as ranges, preferred ranges, or ranges defined by a series of preferred upper limit values and preferred lower limit values, it should be understood as specifically disclosing all ranges formed by any pairing of any range upper limit or preferred value with any range lower limit or preferred value, regardless of whether the ranges are individually disclosed. For example, when ranges "1 to 5" are disclosed, the described ranges should be interpreted as including ranges "1 to 4", "1 to 3", "1 to 2", "1 to 2 and 4 to 5", "1 to 3 and 5", etc. When a numerical range is described herein, unless otherwise indicated, the range is intended to include its end values and all integers and fractions within the range.

Singular forms include plural objects of discussion unless otherwise clearly indicated in the context. The term "optional" or "any one" means that the described items or events which follow may or may not occur, and the description includes the case where the events occur and the case where the events do not occur.

Approximate terms in the description and claims are used to modify quantities, indicating that the present invention is not limited to the specific quantities, but also includes acceptable modified parts close to the quantities without resulting in changes in related basic functions. Accordingly, where a numerical value is modified with "approximately", "about", etc., it is meant that the present invention is not limited to the precise numerical value. In some examples, the approximate expressions may correspond to the accuracy of an instrument that measures the numerical values. In the description and claims of the present application, range definitions may be combined and/or interchanged, unless otherwise indicated that these ranges include all subranges contained therebetween.

In addition, the indefinite articles "a" and "an" before an element or component in the present invention do not limit the quantity requirements (i.e., the number of occurrences) of the element or component. Therefore, "a" or "an" should be interpreted as including one or at least one, and an element or component in the singular form also includes the plural form thereof, unless the number clearly refers to the singular form.

The present invention provides a novel air purification composition with antiviral and bactericidal functions, which at least comprises the following components in percentage by weight: 0.3%-1% of a black poplar essential oil, 0.1%-1% of a tea tree essential oil, 0.1%-0.5% of a *Cupressus funebris* essential oil, 0.1%-1% of an *Artemisia apiacea* essential oil, 0.1%-10% of a *Sophora flavescens* extract, 0.1%-5% of a ginger extract, 5%-30% of a *Cupressus funebris* hydrolate, 0.5%-1% of a hyperbranched amino polymer, 0.5%-5% of a surfactant, and the balance being water.

In some embodiments, it at least comprises the following components in percentage by weight: 0.5%-0.8% of a black poplar essential oil, 0.4%-0.6% of a tea tree essential oil, 0.2%-0.4% of a *Cupressus funebris* essential oil, 0.5%-0.8% of an *Artemisia apiacea* essential oil, 4%-8% of a *Sophora flavescens* extract, 2%-4% of a ginger extract, 14%-22% of a *Cupressus funebris* hydrolate, 0.8%-1% of a hyperbranched amino polymer, 2%-6% of a surfactant, and the balance being water.

In some embodiments, it at least comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The black poplar essential oil in the present invention is an essential oil extracted from Italian black poplar, also known as Italian poplar, which is a large deciduous tree with a long oval crown, a grayish brown bark and is lobated. The leaves are triangular and have a heart shape at the base with 2-4 glandular dots, the length of the leaves is slightly larger than the width, the leaves are dark green and thick in texture. The petiole is flat.

The tea tree essential oil in the present invention is originated from Australia and is an extract of tea trees, and the main chemical components thereof are p-terpinene, dipentene, limonene, cineol, terpinol and cumene.

The *Cupressus funebris* essential oil is an essential oil extracted from *Cupressus funebris*, the main chemical components of the *Cupressus funebris* essential oil are cedrene, sesquiterpene and cedrol. The *Cupressus funebris* hydrolate is an aqueous solution separated from the extraction of the *Cupressus funebris* essential oil.

The *Artemisia apiacea* refers to the dry aboveground part of *Artemisia annua* L. of compositae. The variety has a cylindrical stem, the upper part of which is ramous, and has a length of 30-80 cm and a diameter of 0.2-0.6 cm; the surface is yellowish green or brownish yellow and has longitudinal ridges; and it is slightly hard in texture and is easy to break, and has marrow in the middle of a cross section. The leaves thereof alternate, are dark green or brownish green, easily fragile when huddled up, the complete leaves are tripinnatiparted after being flattened; the lobes and lobules are oblong or long elliptical, with short hairs on both sides. The variety has a special fragrant smell and a slightly bitter taste. It is bitter and pungent in taste and cold in character. It is assigned to liver and gallbladder meridians. The main therapeutic functions thereof are to clear away heat, relieve summer heat, eliminate steam, and stop malaria. It can be used for fever due to summer heat evil, yin-deficiency fever, night fever abating at dawn, bone steaming and consumptive fever, malaria, chills and fever, and jaundice due to damp-heat.

The aboveground part thereof contains terpenes including: artemisinin (qinghaosu, artemisinin, or arteannuin), artemisinin I (qinghaosu I, artemisinin A, or arteannuin A), artemisinin II (qinghaosu II, artemisinin B, or arteannuin B), artemisinin III, i.e., hydrogenated artemisinin, deoxidized artemisinin (qinghaosu III, hydroartemisinin, deoxyartemisinin), artemisinin IV (qinghaosu IV), artemisinin V (qinghaosu V), artemisinin VI (qinghaosu VI), artemisinin C (arteannuin C), which is an isomer of artemisinin B, arteannuin G, deoxyisoartemisinin B (epideoxyarteannuin B), deoxyisoartemisinin C, artemisitene, arteannuic acid (qinghao acid, artemisic acid, or artemisinic acid), dehydroartemisinic acid, epoxyartemisinic acid, 11R-L-dihydroartemisinic acid (11R-dihydroartemisinic acid), methyl artemisinate, artemisinol, norannuic acid, dihydroepideoxyarteannun B, annulide, friedelin, friedelan 3β-ol, etc.; flavonoids including: quercetagetin-6,7,3,4-tetramethylether, chrysosplenol (chrysosplenol D), artemetin, 3-methoxychrysosplenol (chrysolplenetin), 3,5,3-trihydroxy-6,7,4-trimethoxyflavone, 5-hydroxy-3,6,7,4-tetram-ethoxyflavone, casticin, cirsilineol, 5,3-dyhydroxy-6,7,4-trimethoxyflavone (penduletin), 5,7,3,4-tetrahydroxy-dimethoxyflavone (axillarin), cirsiliol, tamarixetin, rhamnetin, quercetin-3-methylether, cirsimaritin, rhamnocitrin, chrysoeriol, 5,2,4-trihydroxy-6,7,5-trimethoxyflavone (5,2,4-trihydroxy-6,2,4-trihydroxy-6,7,5-trimethoxyflavone), 5,7,8,3-tetrahydroxy-3,4-dimethoxyflavone, quercetagetin-3,4-dimethylether, kaempferol, quercetin, luteolin, patuletin, quercetin-3-rutinoside, luteolin-7-O-glycoside, kaempferol-3-O-glucoside (kaempferol-3-O-glucpferol-3-O-glucoside), quercetin-3-O-glucoside, patuletin-3-O-glucoside, 6-methoxykaempferol-3-O-glucoside, etc.; coumarins including: scopoletin, coumarin, 6,8-dimethoxy-7-hydroxycoumarin, 5,6-dimethoxy-7-hydroxycoumarin, scoparon, etc.; volatile oils including: L-camphor, β-caryophellene, isoartemisiaketon, β-pinene, bornyl acetate, 1,8-cineole, carveol (benzylisovaleric acid), β-farnesene, copaene, γ-muurolene, tricyclene, α-pinene, fenchone, artemisa ketone, linalool, isoborneol, α-terpineol, borneol, camphene, myrcene, limonene, γ-terpineol, bornylisovalerate, γ-cadinene, ξ-cadinene, α-elemene, β-elemene, γ-elemene, salicylic acid, β-terpinene, α-thujene, 4-terpineol, 4-terpingyl acetate, linlayl acetate, etc.; others including: palmitic acid, stigmasterol, β-sitosterol, aurantiamideacetate, 5-nonadecylresorcinol-3-O-methylether, nonacosanol, 2-methyltriacosan-8-one-23-ol, hentriacontanyl triacontanoate, 2,29-dimethyltriacontane, annuadiepoxide, ponticaepoxide, and β-glucosidases III having a molecular weight of 150 000 and 100 000 respectively, etc.

The *Sophora flavescens* refers to the dry root of *Sophora flavescens* of the leguminosae. It is cold in character and bitter in taste, and has the effects of clearing heat, eliminating dampness, killing insects and inducing diuresis. The main components of *Sophora flavescens* include matrine, oxymatrine, N-oxysophocarpine, sophoridine, D-allomatrine, D-isomatrine, D-sophoranol, (+) sophoranol N-oxide, L-sophocarpine, L-sophoramine, D-N-methylcytisine, L-anagyrine, and baptifoline. The root also contains a variety of flavonoid compounds: kushenols A, B, C, D, E, F, G, H, I, J, K, L, M, N, and O, kuraridin, kuraridinol, kurarinol, neokurarinol, norkurarinol, isokurarinone, formononetin, kurarinone, norkurarinone, methylkushenol C, lmaackiain, trifolirhizin and rtifolirhizin-6''-O-malonate, kushenin, isoanhydroicaritin, noranhydroicaritin, xanthohumol, isoxanthohumol, and luteolin-7-glucoside. In addition, the root also contains triterpene saponins including: sophoraflavosides I, II, III and IV, soyasaponin I, and quinonoid compound: kushequinone A. The aboveground part contains alkaloids including: matrine, oxymatrine, D-allomatrine, isomatrine, sophoranol, sophoranol N-oxide, anagyrine, baptifoline, L-N-methylcytisine, L-sophocarpine, L-sophoramine, D-N-oxysophocarpine, L-Δ7-dehydrosophoramine, isosophocarpine, L-13,14-dehy-drosophoridine, D-9a-hydroxymatrine, L-9a-hydroxysophocarpine, L-9a-hydroxysophocarpine N-oxide, L-7,8-dehydrosophoramine, L-9a-hydroxysophoramine, a dimer of N-methylcytisine, sophoridine, and D-12-lehmannine. It also contains 2-alkylchromone derivatives, wherein 2-n-heneicosyl-5,7-dihydroxy-6,8-dimethyl chromone and 2-n-tricosyl-5,7-dihydroxy-6,8-dimethylchromone dominate, and 2-n-tridecyl-, 2-n-pentadecyl-, 2-n-heptadecyl-, 2-n-nonadecyl- and 2-n-pentacosyl-5,7-dihydroxy-6,8-dimethyl chromones are also contained.

In some embodiments, a method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness.

In some embodiments, the weight ratio of said clear limewater to said *Sophora flavescens* is 6:1.

The clear limewater in the present invention refers to a saturated calcium hydroxide aqueous solution.

The ginger refers to the fresh rhizome of *Zingiber officinale* Rosc. It is irregularly blocky and slightly flat, and has finger-shaped branches, a length of 4-18 cm and a thickness of 1-3 cm. The surface thereof is yellowish brown or grayish brown and has links, and there are stem marks or buds at the top of the branches. The ginger is fragile in texture, easy to break, light yellow in a cross-section, and has obvious ring-like grains in endodermis, and scattered vascular bundles. It has a special fragrant smell and a pungent taste. It is pungent and tepid in character. It is assigned to lung, spleen and stomach meridians. The main therapeutic functions thereof are to relieve exterior syndrome, dispel cold, warm the middle, stop vomiting, resolve phlegm and relieve cough. It is used for treating common cold due to wind-cold, vomiting due to stomach cold, and cold phlegm cough.

The ginger contains dozens of volatile ingredients including: α-zingiberene, β-santalol, β-phellandrene, β-bisabolene, α-curcumene, zingiberol, perillaldehyde, neral, geranial, 2-caraneol, 3-carol, camphene, β-ocimene, α-bergamotene, β-farnesene, myrcene, β-pinene, 2-borneol, citral, 7-menthene, isofenchyl alcohol, α-farnesene, 1,3,3-trimethyltricyclo[2.2.1.02, 6]heptane, 2,6-dimethyl-6-(4-methyl-3-pentenyl)-bicyclo[3.1.1]-2-heptene, 1,3,3-trimethyl-2-oxabicyclo[2.2.2]octane, 1-(1,5-dimethyl-4-hexenyl)-4-methylbenzene, galanolactone, etc.; and pungent ingredients including: 6-gingerol, 3-gingerol, 4-gingerol, 5-gingerol, 8-gingerol, 10-gingerol, 12-gingerol, 6-gingediol, 4-gingediol, 8-gingediol, 10-gingediol, 6-methylgingediol (6-gingediol), 4-gingediol, 8-gingediol, 10-gingediol, 6-methylgingediol, 4-gingediacetate, 6-gingediacetate, 6-methylgingediacetate, 6-gingerdione, 10-gingerdione, 6-dehydrogingerdione, 10-dehydrogingerdione, 6-acetylgingerol, 6-shogaol, etc. The ginger also contains a variety of amino acids, such as furanogermenone, 2-pipecolic acid and aspartic acid, glutamic acid, serine, etc.

In some embodiments, a method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

In some embodiments, the weight ratio of said ginger extract to said *Sophora flavescens* extract is 1:2.

The hyperbranched amino polymer used in the present invention is an amino-terminated hyperbranched polyamide.

In some embodiments, the content of amino in said hyperbranched amino polymer is 12-16 moles of amino per mole of the hyperbranched amino polymer.

In some embodiments, said surfactant is a mixture of a non-ionic surfactant and an anionic surfactant.

In some embodiments, said nonionic surfactant is selected from at least one of Tween-20, Tween-40 and Tween-60.

In some embodiments, said anionic surfactant is selected from one of sodium dodecyl sulfonate and potassium dodecyl sulfonate.

In some embodiments, said surfactant is a mixture of Tween-20 and sodium dodecyl sulfonate, wherein the weight ratio of Tween-20 to sodium dodecyl sulfonate is 2:1.

In the process of completing the present invention, the inventors have found that when the content of amino group in the hyperbranched amino polymer is 12-16 moles of amino group per mole of the hyperbranched amino polymer, the formaldehyde removal effect can be improved; and the inventors speculated that this may be caused by an interaction between amino group and formaldehyde, which enhances the capture of formaldehyde molecules, thereby improving the formaldehyde eliminating effect of other components. However, after storage for a long period of time since the addition of the hyperbranched amino polymer, the active groups in the hyperbranched amino polymer may change the color of the composition, which affects the experience of users. When extracting *Sophora flavescens* with a citric acid aqueous solution, the inventor misused clear limewater as the citric acid aqueous solution, and unexpectedly found that after soaking and extraction with the clear limewater, *Sophora flavescens* could act to prevent the composition from discoloring, the reason for which may be that the clear limewater promoted the dissolution of effective substances from the *Sophora flavescens*. In order to improve the formaldehyde eliminating effect of the composition, the ratio of the clear lime water to the *Sophora flavescens* is further determined.

The present invention is further defined below in conjunction with particular examples, and unless otherwise specified, all the raw materials are purchased.

Example 1

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness. the weight ratio of said clear limewater to said *Sophora flavescens* is 6:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

Example 2

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness. The weight ratio of said clear limewater to said *Sophora flavescens* is 6:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N101. The content of amino in the hyperbranched amino polymers is 3.5 moles of amino per mole of the hyperbranched amino polymers.

Example 3

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness. The weight ratio of the clear limewater to the *Sophora flavescens* is 1:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

Example 4

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness. The weight ratio of the clear limewater to the *Sophora flavescens* is 10:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

Example 5

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in deionized water for 1 h, heating and refluxing the mixture for 3 h, cooling and then filtering the mixture, and evaporating the filtrate under reduced pressure to dryness.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

Example 6

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched amino polymer, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in aqueous citric acid for 1 h, heating and refluxing the mixture for 3 h, cooling and then filtering the mixture, and evaporating the filtrate under reduced pressure to dryness. The concentration of said citric acid aqueous solution is 4 g/L. The weight ratio of the citric acid aqueous solution to the *Sophora flavescens* is 6:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

Example 7

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 3% of a surfactant, and the balance being water.

The weight ratio of said ginger extract to said *Sophora flavescens* extract is 1:2.

A method for the extraction of said *Sophora flavescens* extract involves: washing *Sophorae flavescentis* clean, grinding the *Sophorae flavescentis* into powder, then soaking the powder in a clear limewater for 1 h, heating and refluxing the mixture for 3 h, cooling and then filtering the mixture, and evaporating the filtrate under reduced pressure to dryness. The weight ratio of said clear limewater to said *Sophora flavescens* is 6:1.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

Example 8

A novel air purification composition with antiviral and bactericidal functions is provided, which comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 3% of a ginger extract, 20% of a *Cupressus funebris* hydrolate, 0.95% of a hyperbranched amino polymer, 3% of a surfactant, and the balance being water.

A method for the extraction of said ginger extract involves: washing ginger clean, cutting the ginger into shreds, refluxing the shreds with a mixed solvent of ethanol and acetic acid for 3 h, cooling and then filtering the resultant, and evaporating the filtrate under reduced pressure to dryness. The weight ratio of ethanol to acetic acid is 5:1.

Said surfactant is a mixture of Tween-20 and sodium dodecyl sulfonate, wherein the weight ratio of Tween-20 to sodium dodecyl sulfonate is 2:1.

The hyperbranched amino polymer is an amino-terminated hyperbranched polyamide, and is purchased from Wuhan Hyperbranched Polymers Science & technology Co., Ltd. under Hyper N103. The content of amino in said hyperbranched amino polymer is 14 moles of amino per mole of the hyperbranched amino polymer.

The preparation method for Examples 1-8 involves mixing the components at room temperature.

1. Formaldehyde Removal Test

A certain volume of chemically pure formaldehyde is injected into a 1 m$^3$ sealed experiment chamber, a fan in the chamber is turned on, and a sample is taken immediately after one hour and tested for the gas concentration in the experiment chamber as the initial concentration. In the 1 m$^3$ sealed experiment chamber, examples 1-8 are respectively sprayed into the chamber, samples are taken immediately after 72 hours and tested for the gas concentration in the experiment chamber to calculate the removal rates thereof. Removal rate=(Initial concentration−Sample concentration)×100%/Initial concentration.

2. Storage Test

The absorbances of Examples 1-8 were measured at 190-800 nm using an ultraviolet-visible spectrophotometer, and the absorbances thereof at a wavelength of 468 nm were recorded as $A_0$, Examples 1-8 were then left to stand in a transparent sealed container for 2 months, the absorbances thereof were measured again at 190-800 nm, and the absorbances thereof at the wavelength of 468 nm were recorded as $A_1$. Color change rate=$(A_1-A_0)/A_0\times100\%$.

The test results thereof are listed in the following table.

TABLE 1

|  | Removal rate | Color change rate |
| --- | --- | --- |
| Example 1 | 99.1% | 0.71% |
| Example 2 | 98.3% | 0.74% |
| Example 3 | 98.1% | 4.3% |
| Example 4 | 97.9% | 5.8% |
| Example 5 | 98% | 12.3% |
| Example 6 | 98.1% | 11.8% |
| Example 7 | 85.2% | 0.72% |
| Example 8 | 95.1% | 12.4% |

Unless otherwise claimed, the use of any and all examples, or exemplary language (e.g., "for example") in the present application is only intended to better illustrate the present invention, but is not intended to limit the scope of the present invention. The language in the description should not be understood as indicating that any non-claimed elements are necessary for the implementation of the present invention.

Preferred embodiments of the present invention, including the best modes to implement the present invention, as known by the inventors, are described in the present application. Modifications to those preferred embodiments would have been obvious to those of ordinary skill in the art upon reading the foregoing description. The inventors expect those skilled in the art to appropriately use such modifications, and the inventors intend to implement the present invention in a manner different from that specifically described herein. Therefore, the present invention includes the implementation of all changes and equivalents, as permitted by applicable laws, of the subject matter set forth in the appended claims which follow. Moreover, the present invention includes any combination of all possible modifications of the elements described above, unless otherwise stated in the present application or clearly contradicted by the context.

The invention claimed is:

1. A novel air purification composition with antiviral and bactericidal functions, characterized in that it at least comprises the following components in percentage by weight: 0.3%-1% of a black poplar essential oil, 0.1%-1% of a tea tree essential oil, 0.1%-0.5% of a *Cupressus funebris* essential oil, 0.1%-1% of an *Artemisia apiacea* essential oil, 0.1%-10% of a *Sophora flavescens* extract, 0.1%-5% of a ginger extract, 5%-30% of a *Cupressus funebris* hydrolate, 0.5%-1% of a hyperbranched polyamide, 0.5%-5% of a surfactant, and the balance being water.

2. The novel air purification composition with antiviral and bactericidal functions of claim 1, characterized in that it at least comprises the following components in percentage by weight: 0.5%-0.8% of a black poplar essential oil, 0.4%-0.6% of a tea tree essential oil, 0.2%-0.4% of a *Cupressus funebris* essential oil, 0.5%-0.8% of an *Artemisia apiacea* essential oil, 4%-8% of a *Sophora flavescens* extract, 2%-4% of a ginger extract, 14%-22% of a *Cupressus funebris* hydrolate, 0.8%-1% of a hyperbranched polyamide polymer, 2%-6% of a surfactant, and the balance being water.

3. The novel air purification composition with antiviral and bactericidal functions of claim 1, characterized in that it at least comprises the following components in percentage by weight: 0.6% of a black poplar essential oil, 0.5% of a tea tree essential oil, 0.3% of a *Cupressus funebris* essential oil, 0.6% of an *Artemisia apiacea* essential oil, 6% of a *Sophora flavescens* extract, 3% of a ginger extract, 20% of a *Cupressus funebris* hydrolate, 0.95% of a hyperbranched polyamide polymer, 3% of a surfactant, and the balance being water.

4. The novel air purification composition with antiviral and bactericidal functions of claim 1, characterized in that a weight ratio of said ginger extract to said *Sophora flavescens* extract is 1:2.

5. The novel air purification composition with antiviral and bactericidal functions of claim 1, characterized in that a method for extraction of said *Sophora flavescens* extract involves: washing *Sophorae flavescentis* clean, grinding the *Sophorae flavescentis* into powder, then soaking the powder in a clear limewater for 1 h to form a mixture, heating and refluxing the mixture for 3 h, cooling and then filtering the mixture to form a filtrate, and evaporating the filtrate under reduced pressure to dryness.

6. The novel air purification composition with antiviral and bactericidal functions of claim 5, characterized in that a weight ratio of said clear limewater to said *Sophora flavescens* is 6:1.

7. The novel air purification composition with antiviral and bactericidal functions of claim 1, characterized in that a method for extraction of said ginger extract involves: washing ginger clean, cutting the ginger into shreds, refluxing the shreds with a mixed solvent of ethanol and acetic acid for 3 h to form a resultant, cooling and then filtering the resultant to form a filtrate, and evaporating the filtrate under reduced pressure to dryness.

8. The novel air purification composition with antiviral and bactericidal functions of claim 1, characterized in that said surfactant is a mixture of a non-ionic surfactant and an anionic surfactant.

9. The novel air purification composition with antiviral and bactericidal functions of claim 8, characterized in that said nonionic surfactant is selected from at least one of polysorbate-20, polysorbate-40 and polysorbate-60.

10. The novel air purification composition with antiviral and bactericidal functions of claim 8, characterized in that said anionic surfactant is selected from one of sodium dodecyl sulfonate and potassium dodecyl sulfonate.

* * * * *